United States Patent [19]

Brewer

[11] Patent Number: 5,034,331

[45] Date of Patent: Jul. 23, 1991

[54] COMPOSITIONS AND METHODS FOR CULTURING MICROORGANISMS REQUIRING SPECIAL GASEOUS ENVIRONMENTS

[75] Inventor: John H. Brewer, Abilene, Tex.

[73] Assignee: Fairleigh Dickinson Laboratories, Inc., Abilene, Tex.

[21] Appl. No.: 763,530

[22] Filed: Aug. 8, 1985

Related U.S. Application Data

[63] Continuation of Ser. No. 327,369, Dec. 4, 1981.

[51] Int. Cl.$^5$ ............... C12M 1/22; C12M 3/00; C12M 3/04
[52] U.S. Cl. .................... 435/298; 435/297; 435/284; 435/285
[58] Field of Search ............... 435/801, 253, 243, 297, 435/298, 284

[56] References Cited

U.S. PATENT DOCUMENTS

| | | | |
|---|---|---|---|
| 2,348,448 | 5/1944 | Brewer | 435/801 |
| 2,874,091 | 2/1959 | Fisk | 195/139 |
| 4,241,186 | 12/1980 | Roth | 435/243 |
| 4,329,431 | 5/1982 | Youssef | 435/253 |

OTHER PUBLICATIONS

*Manual of Clinical Microbiology,* (1974), p. 882, American Society for Microbiology.

*Primary Examiner*—Elizabeth C. Weimar
*Assistant Examiner*—Gail Poulos

[57] ABSTRACT

Metal hydrosulfites are found to be advantageous reducing agents for removing oxygen from contained atmospheres. When dissolved in alkaline aqueous gels, the hydrosulfites are effective to initiate and maintain anaerobiosis for culturing oxygen-sensitive microorganisms and animal tissues.

5 Claims, 1 Drawing Sheet

U.S. Patent   July 23, 1991   5,034,331
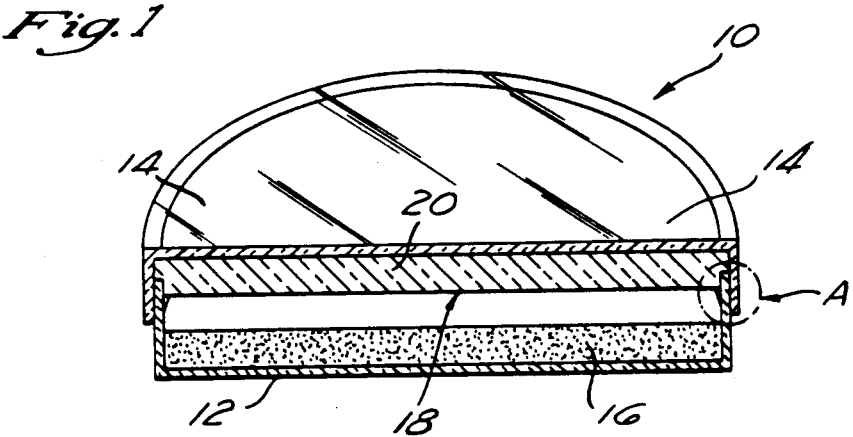
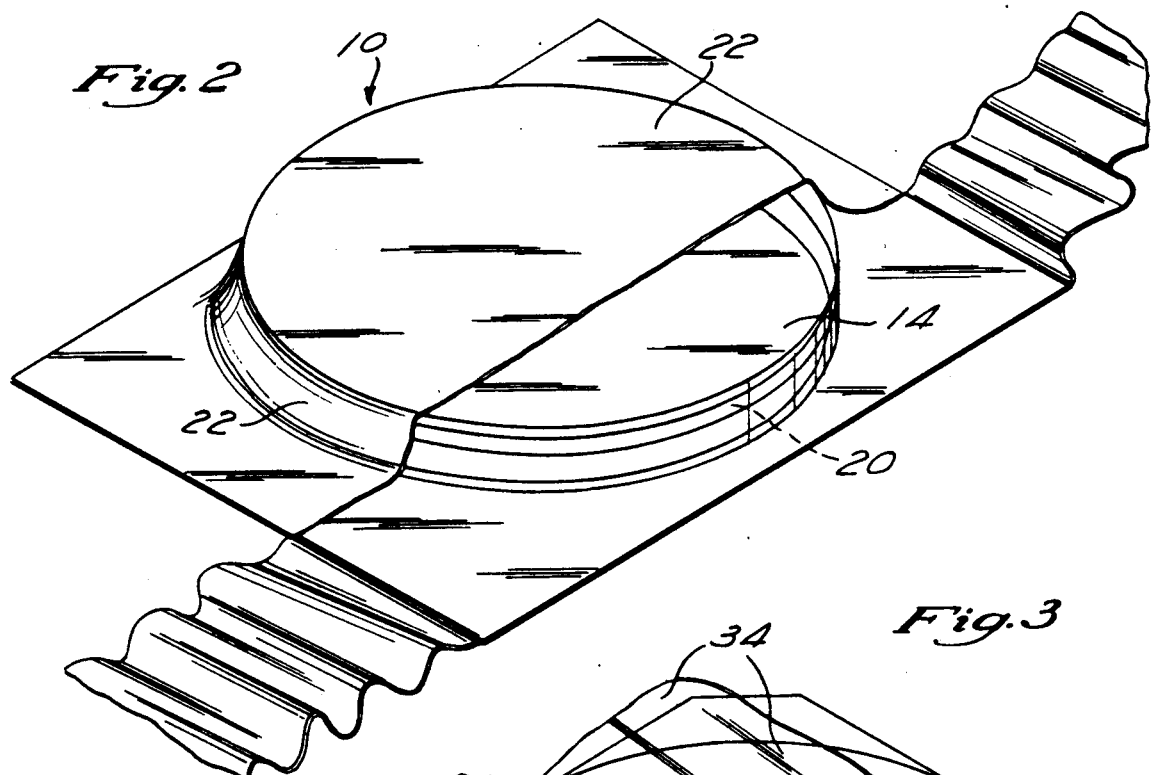
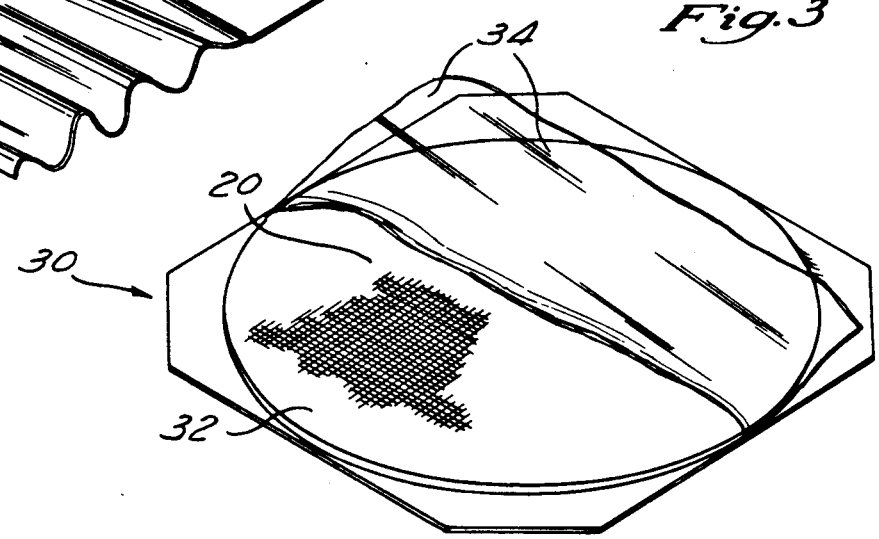

COMPOSITIONS AND METHODS FOR CULTURING MICROORGANISMS REQUIRING SPECIAL GASEOUS ENVIRONMENTS

This is a continuation of application Ser. No. 327,369, filed Dec. 4, 1981.

BACKGROUND OF THE INVENTION

1. Field of the Invention

The invention relates to chemical compositions and their use in the culturing of microorganisms and tissues and more particularly relates to compositions and methods useful for culturing oxygen sensitive (anaerobic and microaerophilic) microorganisms, and microorganisms and tissues requiring special gaseous environments.

2. Brief Description of the Prior Art

The prior art literature is replete with descriptions of methods and apparatus useful for culturing oxygen sensitive microorganisms. Representative of such descriptions are those found in the U.S. Pat. Nos. 2,348,448; 2,361,992; 2,463,143; 3,165,450; 3,208,909; 3,248,302; 3,483,089; 3,913,564; 4,030,978; 4,033,826; 4,038,148; and 4,200,610.

In spite of the many prior art methods and the large number of different apparatus previously described for culturing oxygen sensitive microorganisms, none have been completely satisfactory for all circumstances of needs and uses For example, a large number of methods and apparatus depend on the generation and use of hydrogen gas to combine with and thereby remove oxygen from the atmosphere; see for example U.S. Pat. No. 3,483,089. Of course, hydrogen gas poses the hazard associated with any explosive gas. In addition, relatively expensive catalysts may be required to satisfactorily promote the desired reduction of oxygen.

The apparatus and method of the present invention are not dependent on the generation or use of explosive gases or exotic catalysts and therefore obviate these problems of the prior art.

Many of the prior art methods of maintaining anaerobiosis within the confines of a culture environment depend on the use of special laboratory hardware such as anaerobic chambers, anaerobe jars and the like. In U.S. Pat. No. 2,348,448 there is described a modified Petri type of culture dish for use in culturing oxygen sensitive microorganisms. The cover of the dish is modified by depression of the central portion towards the bottom of the dish. This greatly reduces the air space within the closed dish and above any nutrient media disposed in the dish bottom. A deeper annular depression near the peripheral rim of the cover contacts the upper surface of the nutrient media to seal the edges of the air space. The air space, sealed off, is about 1 mm deep. Oxygen in the air space is removed chemically by the presence of a reducing agent incorporated in the nutrient media (anaerobic agar).

Those individuals responsible for budgeting laboratory finances appreciate that the above-described special or modified forms of apparatus are relatively expensive. In the method of the present invention, using the compositions and apparatus of the invention, small laboratories with limited funds need not invest in the more expensive prior art equipment in order to carry out anaerobic microbiology culturing. Instead, they may use the ordinary, commercially available Petri dish with the compositions of the invention. No modification of the standard Petri dish is required. No special seals or "O" rings need be purchased to seal the culturing environment. In fact, the microbiologist need not modify either the equipment normally on hand in the laboratory or the technique of culturing in order to practice the present invention. This latter point is of particular importance since it means that laboratory personnel need not undergo specific training or retraining to practice the method of the invention.

The U.S. Pat. No. 3,248,302 includes in its description of the art a discussion of the so-called "single plate method" of growing strictly anaerobic bacteria. The term "single plate method" refers in particular to the use of a sealed Petri dish containing a nutrient medium, the surface of which is inoculated with the anaerobe desired for culture. After discussing in detail the problems associated with all the prior art methods of culturing anaerobes, including the single plate method, the patentee states that "the criteria for an ideal single plate method of growing bacteria under anaerobic conditions are generally as follows: that the method can be used routinely, that anaerobiosis (removal of oxygen) or other desired atmospheric conditions will result rapidly upon closing the culture dish or plate; that in the practice of the method, any culture medium suitable to culturing the bacteria in a standard size Petri dish (plate) can be used; and that no reducing agents toxic to bacteria need be used". The patentee meets this criteria in his own invention by providing a special, thin elastic seal member for fitting between the lid and the base components of a conventional Petri dish. In other words, the patentee modifies the Petri dish with a special seal component.

In the present invention, the desired criteria established by the patentee in U.S. Pat. No. 3,248,302 is also fully met, but in a simpler fashion without the need for a special elastic membrane component to function as a seal, i.e.; without the need to modify a Petri dish.

Sodium hydrosulfite has long been used as an additive or agent in food preservation and is recognized as an antimicrobial; see for example Kirk-Othmer, Encyclopedia of Chemical Technology, Second Edition, Vol. 10, page 13. It has also been used as an ingredient of the well-known Clausen medium.

Clausen medium [dithionite-thioglycollate (HS-T) broth]is a well-known liquid medium used by microbiologists for sterility testing. It includes with a long list of nutritional ingredients in agar, 0.4 gms./liter of sodium hydrosulfite. The medium has a pH of about 7.1 and is sterile by virtue of autoclaving at 121° C. for at least 15 minutes. Autoclaving conditions are known to promote a rapid oxidation or degradation of sodium hydrosulfite and its initial oxidation product sodium metabisulfite.

Under the conditions of use in the present invention, sodium hydrosulfite does not function as an antimicrobial agent and does not appear to generate sulfur dioxide gas,

SUMMARY OF THE INVENTION

The invention comprises a composition for reducing atmospheric oxygen, which comprises; a metal hydrosulfite in an aqueous gel having a pH above about 7.5.

The term "aqueous gel" is used herein in its broadest sense as embracive of colloidal solutions or suspensions in their solid phase.

The invention also comprises intermediate compositions and use of the compositions of the invention in processes for culturing oxygen sensitive microorganisms, i.e.; anaerobic and microaerophilic microorganisms and other microorganisms which require special atmospheric conditions.

Compositions and methods of the invention are useful to remove atmospheric oxygen from closed vessels and containers, particularly in conjunction with the culturing of oxygen sensitive microorganisms and for the production of additional atmospheres such as carbon dioxide.

BRIEF DESCRIPTION OF THE DRAWINGS

FIG. 1 is a cross-sectional, side elevation of a Petri dish, the lid of which bears on the inner surface a composition of the invention for maintaining anaerobiosis within the confines of the dish.

FIG. 2 is a view-in-perspective of a pre-packaged Petri dish lid, partially cut-away to show the lid containing a composition of the invention.

FIG. 3 is a view-in-perspective of a pre-packaged composition of the invention, opened to show the packaged composition on a support surface and adapted for use in removing oxygen from sealed containers.

DETAILED DESCRIPTION OF THE PREFERRED EMBODIMENTS OF THE INVENTION

The compositions of the invention comprise a metal hydrosulfite dissolved or suspended in an aqueous gel having a pH value above about 7.5. Metal hydrosulfites are a well-known class of compounds as are methods of their preparation. Representative of known metal hydrosulfites are sodium hydrosulfite (also known as sodium dithionite) and zinc hydrosulfite (also known as zinc dithionite).

The metal hydrosulfites are generally readily dissolved in water and in aqueous solution are advantageously incorporated in a gel. Aqueous gels are readily formed by the addition of a gellant to the water, before, during or after dissolution of the metal hydrosulfite.

Aqueous gels employed in the method and the compositions of the invention may be based on organic or inorganic gellants. Representative of organic gellants and organic gels are colloidal mixtures of agar, agarose, carrageen, gum traganth, gum arabic and the like. Organic gels also include aqueous dispersions of synthetic polymers such as styrene-butadiene copolymers, polystyrene, polyolefins, and the like (referred to at times as latices). Inorganic gellants and aqueous inorganic gels are represented by colloidal mixtures of aluminum hydroxide, smectite types of natural and artificial clays and the like. Preferably the gels will be optically transparent, at least in depths of up to about 10 to 15 mm. This is not an absolute necessity however.

Preferably the gel compositions of the invention will have sufficient consistency to remain immobile when placed in a relatively thin layer on an inverted support. Advantageously, a gel strength within the range of from about 170 to about 350 gms./cm$^2$, most preferably 180 to 190 gms./cm$^2$ (determined by ASTM method D-217) will characterize in part preferred compositions of the invention.

A preferred aqueous gel is one based on agar as a gellant. Unexpectedly good oxygen removal efficiency is associated with compositions of the invention which employ agar as the gellant. This is unexpected because agar based gels have been thought, prior to the present invention, to resist and inhibit diffusion of gases such as air and molecular oxygen within the gel; see U.S. Pat. No. 4,030,978. As a means of removing oxygen from atmospheric gases, diffusion of the oxygen into and through the gel compositions of the invention is important to obtain efficient and quick removal of the oxygen.

The aqueous gel compositions of the invention are also characterized in part by a pH above about 7.5, preferably within the range of from about 7.5 to about 10.0. At the specified pH, the growth of most microorganisms on the gel surfaces or within the body of the gel is inhibited. A jejune environment results in or on the preferred gel surface. This is desirable since it obviates the potential for contaminating a desired culturing of flora of oxygen-sensitive microorganisms and eliminates a need to subject the compositions of the invention to a separate sterilization procedure such as autoclaving. Experience has shown that the compositions of the invention may be exposed to the atmosphere in a microbiology laboratory environment for upwards of several hours and then introduced into a closed Petri dish containing a nutrient agar inoculated with an anaerobe, without itself supporting the growth of a microorganism during incubation of the inoculant.

At the specified pH, it appears also that the oxidation product(s) of the metal hydrosulfite does not include sulfur dioxide. In acid pH solutions, the oxidation of the metal hydrosulfite does ultimately result in the generation of sulfur dioxide, which is of course a biocide and to be avoided if one wishes to grow viable microorganisms.

The desired alkaline pH of normally acid or neutral aqueous gels may be obtained by adjustment, i.e.; the addition of basic materials such as sodium hydroxide, sodium carbonate and the like. Preferably, adjustment when required is obtained by the addition of sodium bicarbonate. The sodium bicarbonate in an aqueous environment slowly degrades to yield carbon dioxide gas, which may be a desirable gas presence for the culturing of certain anaerobes. It also provides a gaseous replacement for the volume of oxygen removed from the culturing vessel as will be described more fully hereinafter. The basic materials may be added to the gel compositions of the invention in proportions sufficient to make the desired pH adjustment and to generate carbon dioxide when desired.

A number of other additives may be included in the compositions of the invention without interferring with its desired oxygen removing behavior. Representative of such additives which are advantageously included in the compositions of the invention are bacteriostatic agents such as Merthiolate, phenyl mercuric nitrate and the like which may be added to the compositions of the invention in bacterial growth inhibiting proportions to inhibit the growth of bacteria to which the compositions may be exposed prior to or during use. Other useful additives to the compositions of the invention include humectants such as glycerol, low molecular weight polyethylene glycols such as carbowax 400 (Union Carbide Corp.) and the like. Humectants retard the loss of moisture from the compositions of the invention.

It should be noted that preferred compositions of the invention do not contain ingredients which would promote growth of a microorganism. This is important. To avoid contamination of a culture by overgrowth of organisms which might be stimulated to grow by the composition, nutrients are avoided as ingredients. The preferred compositions may be described as a jejune environment which will not promote growth of microorganisms.

The compositions of the invention may be prepared by dissolving the metal hydrosulfite in an aqueous gel. In a preferred method of preparation, sufficient of a gellant such as agar is dissolved in boiling water, to form a gel upon cooling of the resulting solution to room temperatures. The hot solution is cooled to a temperature of circa 40 to 45° C. and there is then dissolved in the warm solution any desired proportion of the metal hydrosulfite. The solution may then be pH adjusted, preferably by the addition of sodium bicarbonate and allowed to cool to room temperature, whereby gellation occurs.

Alternatively, the gellant, metal hydrosulfite and pH controlling additive may be pre-mixed and then the mixture dissolved in warm water. Upon cooling to room temperature there is formed the compositions of the invention. A preferred composition of the invention for culturing anaerobes contains from about 0.75 to 2.0 percent by weight of metal hydrosulfite such as sodium hydrosulfite in a water solution gelled by the presence of from 1.0 to 2.0 percent by weight of a gellant such as agar.

Referring now to the accompanying drawings, the invention will be further described in reference to certain articles of the invention. FIG. 1 is a cross-sectional, side elevation of a Petri dish 10 which may be any of the commercially available Petri dishes. Dish 10 comprises a lower base 12 and a slightly larger diameter, covering lid 14. About a third of the base 12 contains a nutritive medium 16 such as blood agar for the support and colonization of microorganisms. Above the medium 16 and separating the lid 14 from the medium 16 is a gas space 18, which is in direct contact with a composition 20 of the invention disposed on the inner surface of the lid 14. In use, the dish 10 is initially in an open condition with the nutrient composition 16 disposed on the bottom of the base 12 and ready to be inoculated with a microorganism for culturing.

The microbiologist usually closes a Petri dish by first placing the lid 14 in an inverted position on a flat surface while holding the base 12 in the left hand to, as is customary, leave the operator with a free hand to hold an inoculating needle, etc. In the inverted position, the lid 14 can receive a pour of a melted composition 20 of the invention. Upon standing for a few moments the poured material will solidify (gel) and the lid is ready to receive the base 12 or dish component in an inverted position, following inoculation of the surface of the nutrient 16. The rim of inverted base 12 forms a hermetic seal with the composition 20 of the invention, isolating and closing the space 18. The hermetic seal may be seen in the zone A identified in FIG. 1. Thus, the composition 20 acts as a sealant to hermetically seal space 18.

In the closed condition as shown in FIG. 1, the metal hydrosulfite dispersed in gel composition 20 reduces the oxygen present in space 18. When sufficient metal hydrosulfite is present to reduce all oxygen level sufficiently to allow growth of fastidious anaerobes, such occurs within about 24 hours (overnight) at room temperatures. When an oxygen indicator is placed in the dish 12, such will show the absence of oxygen after this period of time. Oxygen indicators are well known and include for example reazurin, methylene blue and the like which have characteristic colors in the presence and/or absence of gaseous oxygen. When the nutrient media 16 is blood agar, absence of oxygen in the space 18 will also be indicated by the characteristic darkening of the blood agar.

Following inoculation and closing of the dish 10, the unit is subjected to incubation to grow the inoculant. Growth may be observed through an optically transparent lid 14 when the preferred optically transparent gel composition 20 is used. When the composition 20 is not optically transparent, one may elect to pour it only around the outer periphery of the inverted lid 14, leaving the center free and a window for observation of the interior of dish 10.

The quantity of gel 20 required to remove a given amount of oxygen from the air in space 18 will of course depend on the proportion of metal hydrosulfite present in the gel 20. The quantity of gel 20 required may be readily determined by those skilled in the art, by simple calculation. Although we are not to be bound by any theory of operation, it is believed that the metal hydrosulfite in the compositions of the invention reduces the atmospheric oxygen in the course of being oxidized to the corresponding metabisulfite, according to the reaction scheme illustrated by the formulae:

$$2Na_2S_2O_4 + O_2 \rightarrow 2Na_2S_2O_5$$

wherein sodium hydrosulfite represents a metal hydrosulfite. As shown in the formulae, 2 moles of hydrosulfite are required to remove a mole of oxygen present in the space 18. In general, a stoichiometric excess of the metal hydrosulfide is advantageous to assure the removal of all oxygen from space 18 and to permit reopening and resealing of the dish 10 a number of times.

When it is desired to culture microaerophils, there can be only a single use of the dish 10 and the quantity of gel 20 employed will be sufficient to provide enough metal hydrosulfite to remove only part of the oxygen contained in gas space 18. In general, microaerophiles culture satisfactorily under atmospheres containing from about 4 to about 10 percent (by volume) of oxygen. Those skilled in the art can readily calculate the quantity of composition 20 required to reduce the concentration of oxygen in space 18 to the desired range.

FIG. 2 is a view-in-perspective of a pre-packaged Petri dish lid 14 containing a composition of the invention 20. The lid 14 with contained composition 20 is hermetically sealed in a blister-type package 22 (shown partially cut-away to show the contained lid 14). The hermetically sealed and packaged lid 14 containing pre-disposed composition 20 is stable for at least a year when stored at room temperature (circa 26° C.). When desired for use, the package 22 may be opened and the lid 14 used substantially as described above, but without the need of melting and pouring the composition 20 which has been predisposed in the lid 14.

FIG. 3 is a view-in-perspective of a pre-packaged composition 20 of the invention, carried on a substrate 32 to form an oxygen removing article 30 hermetically sealed in a blister-type of package 34 (shown peeled partially open). The substrate 32 can be any solid or porous surface, such as, for example, a woven mesh of fiberglass, other textile, polymeric resin, etc. When fashioned to an appropriate size, the article 30 of FIG. 3 can be inserted within a sealable vessel, to remove oxygen from the contained atmospheric air. For example, fashioned to close the mouth of a conventional anaerobe jar such as shown in U.S. Pat. 3,483,089, the article 30 can be inserted in such jars. When sealed inside the jars, the composition 20 will act to remove the contained oxygen in the same manner described above in relation to the composition 20 disposed in a Petri dish lid 14.

The following examples show the manner and process of making and using the invention and set forth the best mode contemplated by the inventors for carrying out the invention but are not to be construed as limiting. All parts are by weight unless otherwise indicated.

EXAMPLE 1

An appropriate vessel is charged with deionized water and the charge heated to a temperature of 100° C. To the hot water there is added with stirring sufficient agar (powdered) to make a 1.5 percent solution. The solution is allowed to cool to a temperature of circa 45° C. and there is then added with stirring to the solution, 1.0 percent by weight of sodium hydrosulfite and sufficient sodium bicarbonate to adjust the pH of the solution to 8.0. The resulting solution is then poured in the open lids of a series of Petri dishes (30 ml.) and allowed to cool to room temperature to obtain a gel. A number of the lids are used to close and seal a number of Petri dish bottoms, containing about 25 ml of blood agar, the surface of which was inoculated with a number of different anaerobic microorganisms. No special seal or sealing device is required, the juncture between the lid and the bottom being sealed by the gel composition. Over a period of 24-48 hours, oxygen in the space between the gel composition and the blood agar (a volume of about 60 ml.) is indicated by a noticeable darkening of the blood agar (as oxygen is removed from the oxygenated blood cells) and the development of a vacuum in the closed Petri dish. After 36 hours, visual observation indicates satisfactory growth of the anaerobes, including *Clostridium novyi.*

EXAMPLE 2

Repeating the procedure of Example 1, supra, but adding 0.1 percent of the sodium hydrosulfite instead of 1.0 percent as used in Example 1, a partial removal of oxygen occurs, from the space between the gel composition of the invention and the blood agar. The air in the space contains about 6 to 8 percent (by volume) of oxygen after the same 24-48 hours and after 36 hours, visual observation indicates satisfactory growth of microaerophiles such as *Campylobacter fetus,* when the blood agar surface is inoculated with that organism.

EXAMPLE 3

The procedure of Example 1, supra., is repeated except that no sodium hydrosulfite is added to the cooled solution as was done in Example 1. Over a period of 24-28 hours, oxygen remains in the space between the blood agar and the gel composition as indicated by the bright red color of the blood agar. However, analysis of the gas in the space indicates a carbon dioxide content of about 10 percent. After about 36 hours, visual observation indicates satisfactory growth of *Neiserria gonorrhea* microorganisms.

The above Example 3 shows a modification of the compositions of the invention to provide a gaseous environment favorable to the culturing of carbogenophilic microorganisms.

What is claimed is:

1. Apparatus for the culturing of oxygen sensitive microorganisms, which comprises;

a tube having a closed end and an open end and a sidewall joining the ends, said ends and said sidewall together defining an interior bore;

a removable lid for closing the open end of the tube;

means between the lid and the sidewall for hermetically sealing the bore; and a composition which consists essentially of a metal hydrosulfite dissolved in an aqueous gel having a pH of from about 7.5 to about 10.0 and positioned within the bore;

said gel having a jejune environment on the surface thereof.

2. The apparatus of claim 1 wherein the means for hermetically sealing is an aqueous gel.

3. The apparatus of claim 1 wherein the tube and the lid together consists of a Petri dish.

4. The apparatus of claim 1 hermetically sealed in an air impervious package.

5. The apparatus of claim 1 wherein the metal hydrosulfite is sodium hydrosulfite.

* * * * *